(12) United States Patent
Diem

(10) Patent No.: US 6,947,817 B2
(45) Date of Patent: Sep. 20, 2005

(54) NON-INTRUSIVE DIAGNOSTIC TOOL FOR SENSING OXYGEN SENSOR OPERATION

(75) Inventor: Earl D. Diem, Ortonville, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/700,007

(22) Filed: Nov. 3, 2003

(65) Prior Publication Data

US 2005/0096806 A1 May 5, 2005

(51) Int. Cl.$^7$ .......................................... G06F 19/00
(52) U.S. Cl. .................... 701/34; 701/29; 701/107; 340/438
(58) Field of Search ................. 701/29, 33–35, 701/107, 109; 340/438, 439

(56) References Cited

U.S. PATENT DOCUMENTS

| | | | |
|---|---|---|---|
| 4,839,811 A * | 6/1989 | Kanegae et al. ............... 701/31 |
| 4,928,518 A * | 5/1990 | Tamura ....................... 73/117.3 |
| 5,005,129 A * | 4/1991 | Abe et al. ..................... 701/31 |
| 5,214,582 A * | 5/1993 | Gray ............................ 701/33 |
| 5,278,508 A * | 1/1994 | Bowman ..................... 324/384 |
| 5,357,791 A * | 10/1994 | Gee et al. ................... 73/118.1 |
| 5,585,552 A * | 12/1996 | Heuston et al. ............... 73/116 |
| 5,729,452 A | 3/1998 | Smith et al. |
| 5,801,295 A * | 9/1998 | Davey et al. ................. 73/1.06 |
| 5,835,871 A | 11/1998 | Smith et al. |
| 5,928,303 A * | 7/1999 | Sakai ......................... 701/109 |
| 6,052,631 A | 4/2000 | Busch et al. |
| 6,285,931 B1 | 9/2001 | Hattori et al. |
| 6,339,736 B1 | 1/2002 | Moskowitz et al. |
| 6,430,164 B1 | 8/2002 | Jones et al. |
| 6,449,539 B1 * | 9/2002 | Ohno et al. .................... 701/31 |
| 6,529,808 B1 | 3/2003 | Diem |
| 6,604,033 B1 * | 8/2003 | Banet et al. ................... 701/33 |
| 6,611,740 B2 * | 8/2003 | Lowrey et al. ............... 701/29 |
| 6,688,163 B2 * | 2/2004 | Fujino et al. ................. 73/116 |
| 2003/0182994 A1 | 10/2003 | Huller et al. |

FOREIGN PATENT DOCUMENTS

| | | |
|---|---|---|
| DE | 100 24 190 A1 | 1/2001 |
| GB | 2 350 443 A | 11/2000 |
| GB | 2 364 577 A | 1/2002 |
| WO | WO-02/14828 A2 | 2/2002 |
| WO | WO-02/014828 A3 | 2/2002 |

OTHER PUBLICATIONS

EPA Publication entitled "Performing Onboard Diagnostic System Checks as Part of a Vehicle Inspection and Maintenance Program" dated Jun. 2001.
European Search Report (3 pages).

* cited by examiner

Primary Examiner—Gary Chin
(74) Attorney, Agent, or Firm—Stefan V. Chmielewski

(57) ABSTRACT

A diagnostic testing system for a vehicle includes an oxygen sensor, an analyzer having a user interface, and a communications link between the analyzer and the vehicle to obtain data from the oxygen sensor. A diagnostic heuristic is used to analyze the data and confirm proper operation of the sensor; and an output is generated by said diagnostic heuristic to the user interface.

15 Claims, 10 Drawing Sheets

NON-INTRUSIVE DIAGNOSTIC TOOL FOR SENSING OXYGEN SENSOR OPERATION

TECHNICAL FIELD

The present invention relates to oxygen sensors and in particular, to a system and method for automating and standardizing the diagnostic testing of oxygen sensors.

BACKGROUND OF THE INVENTION

An oxygen senor monitors the ratio of oxygen to gasoline in a vehicle. If there is less oxygen present in the ratio, fuel will remain after combustion. This results in a rich mixture. Rich mixtures create pollution due to the remaining unburned fuel. If there is an excess of oxygen present in the ratio a lean mixture exists. Lean mixtures also tend to produce pollutants. Moreover, lean mixtures may cause poor engine performance and possibly engine damage. In determining whether a rich or lean mixture is present, the oxygen sensor undergoes a chemical reaction that generates a voltage. In one embodiment of a known sensor, rich mixtures have a voltage reading in the range of 450 millivolts (mV) or higher, while lean mixtures have a reading in the range of 449 millivolts or lower. In ideal operating conditions, the oxygen sensor should have an average high and low reading of 450 millivolts at idle or at steady cruise operations.

The oxygen sensor is part of the emissions control system. Positioned in the exhaust system to sample exhaust, it typically is connected to feed data to a powertrain control module (PCM). The data received from the oxygen sensor provides the PCM with input that may be used to calculate the efficiency of the cylinder burn process. To protect the integrity of the catalytic converter and to provide the greatest amount of vehicle performance, the PCM constantly adjusts fuel delivery to the cylinders based upon the input from the oxygen sensor. The PCM expects the oxygen sensor to pass the median voltage a certain number of times and within a pre-determined period. Thus, oxygen sensors may be a source of information regarding the vehicle's performance. However, there is no standardized or automated process for verifying the operation of the oxygen sensor during diagnostic testing. As a result, working oxygen sensors may be replaced during service because the technician may not properly conduct diagnostic testing on the oxygen sensor.

SUMMARY OF THE INVENTION

In one aspect of the invention, a diagnostic testing system for a vehicle includes an oxygen sensor, an analyzer having a user interface, and a communications link between the analyzer and the vehicle to obtain data from the oxygen sensor. A diagnostic heuristic is used to analyze the data and confirm proper operation of the sensor; and an output is generated by the diagnostic heuristic to the user interface.

BRIEF DESCRIPTION OF THE DRAWINGS

The present invention will now be described, by way of example, with reference to the accompanying drawings, in which.

DESCRIPTION OF THE PREFERRED EMBODIMENT

The present invention is directed towards a system and method to non-intrusively conduct diagnostic testing to determine the performance of an oxygen sensor ("oxygen sensor") positioned in the exhaust stream of an internal combustion engine, which is typically running while the test is undertaken. The system and method guides a technician through various inspection processes that result in diagnostic testing of the oxygen sensor. During any particular inspection process, the system collects and records data received from the oxygen sensor as well as optionally from other vehicle systems such as engine RPM and engine throttle position. Once a particular step in the inspection method is completed, the system will analyze the collected data to determine the next step in the inspection process.

I. System Overview

Figure 1:
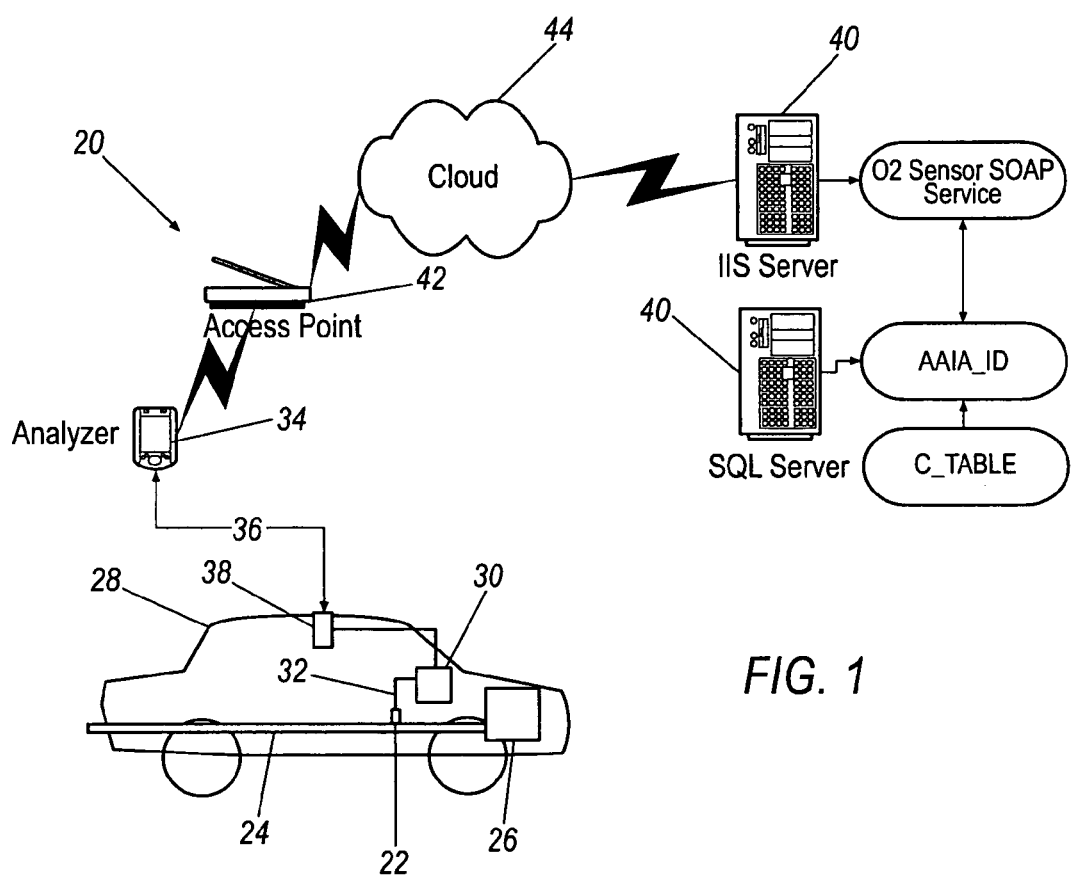
FIG. 1 illustrates an environmental view of an oxygen sensor diagnostic system.

FIG. 1 provides an environmental view of one exemplary system 20 of the present invention. An oxygen sensor 22 is located in the exhaust stream 24 of an internal combustion engine 26 associated with a vehicle 28. The oxygen sensor 22 is part of the emissions control system and is in communication with and typically feeds data to an on-board vehicle control module 30 such as the powertrain control module (PCM) on-board diagnosis (OBD) system. While the discussion below focuses generally on the PCM, any appropriate or combination of modules may be used.

The purpose of the oxygen sensor 22 is to provide the PCM 30 with input that may be used to calculate the efficiency of the cylinder burn process. The PCM 30 uses this information to calculate and adjust short-term fuel calculations during "closed loop" engine operations.

For the purpose of testing the operation of the oxygen sensor 22, it is possible to connect an analyzer 34 such as a hand held computer to the vehicle by way of an interface cable 36. The analyzer 34 typically includes an input mechanism such as microphone, mouse, keyboard, or touch screen, and an output mechanism such as a screen or a sound system. The analyzer 34 utilizes a software system to facilitate a data interface between the analyzer and the vehicle, data communication from the vehicle, and even diagnostic analysis in the form of a diagnostic heuristic in the manner discussed below.

In a preferred embodiment, the analyzer 34 is connected using a communications link such as a serial data bus 38 associated with a vehicle bus interface, that in turn is connected preferably in real time to the various vehicle systems such as the PCM 30 and ultimately to the oxygen sensor 22. In some embodiments, data may be read directly from the PCM. Thus, the oxygen sensor 22 may be tested without disturbing any sensor connectors or wiring associated with the oxygen sensor itself to confirm that not only is the oxygen sensor operational, but so is the entire interface between the sensor and related vehicle components such as the PCM 30. At the same time that data is collected from the oxygen sensor, it is possible to generally simultaneously collect information from other vehicle systems such as engine RPM and throttle position such that these other readings may be correlated using the same time stamp by the analyzer 34 to the readings received from the oxygen sensor 22. Thus, for example, voltage from the oxygen sensor can be correlated with a corresponding engine RPM or throttle position occurring at the same time that the voltage was measured.

In turn the analyzer 34 is in selective communication with one or more servers 40. Server 40 typically contributes to operation of the diagnostic heuristic as discussed below. In the illustrated embodiment, the analyzer 34 has a wireless interface with an access point 42, and then by means of a data transmission cloud 44, which may be a mixture of wired and wireless communication protocols, the information is exchanged with the server 40. Of course, other approaches may be used including the storing of data on the analyzer 34 until the computer is docked with a fixed unit used to transmit data; a data mechanism such as a data card or floppy associated with the analyzer 34 such may be used to complete data transmission between the analyzer and the server 40; or the complete diagnostic analysis may take place within the analyzer itself using a diagnostic heuristic as part of the software system.

Before any testing can be done, however, it is necessary for the oxygen sensor 22 to be within its anticipated operational environment. For one known sensor, known as the zirconia oxygen sensor 22, this means the sensor must first be heated up to at least a minimum operational temperature such as 574 degrees F. (Sensor_Temp). At this temperature or higher, the oxygen sensor 22 produces an analog voltage by comparing the ambient oxygen (A02) level to the amount of oxygen available in the exhaust (EXO2) stream post combustion. The greater the difference between A02 and EXO2, the more voltage is produced. For one known zirconia oxygen sensor 22, the voltage can vary between approximately 0V and 1.125V. For another known zirconia oxygen sensor 22, the voltage can range between 0V and up to 1.5V in Death Valley, 1.1V at Sea Level and 0.9V in Denver, Colo.

The PCM 30 is calibrated in such a way that a bias voltage is established, which represents median between "large" oxygen content (0–449 mV) known as a lean mixture and "small" oxygen content (451 mV +), which are known as rich mixtures. In the illustrated embodiment, 450 mV represents a calibrated median bias voltage (Cross_Voltage). Thus, 0–449 mV represents "large" oxygen content and anything over 451 mV represents "small" oxygen content.

To protect the integrity of catalytic converter associated with the exhaust systems of automotive vehicles sold in many countries and to provide the operator with the greatest amount of vehicle performance, the PCM constantly adjusts fuel delivery to the cylinders via Short Term Fuel Trim Calculations and by controlling both Injector Pulse Width and Ignition Dwell Time so that the average high and low value is the median voltage level (e.g., 450 mV) at idle or steady cruise operations.

Figure 2:
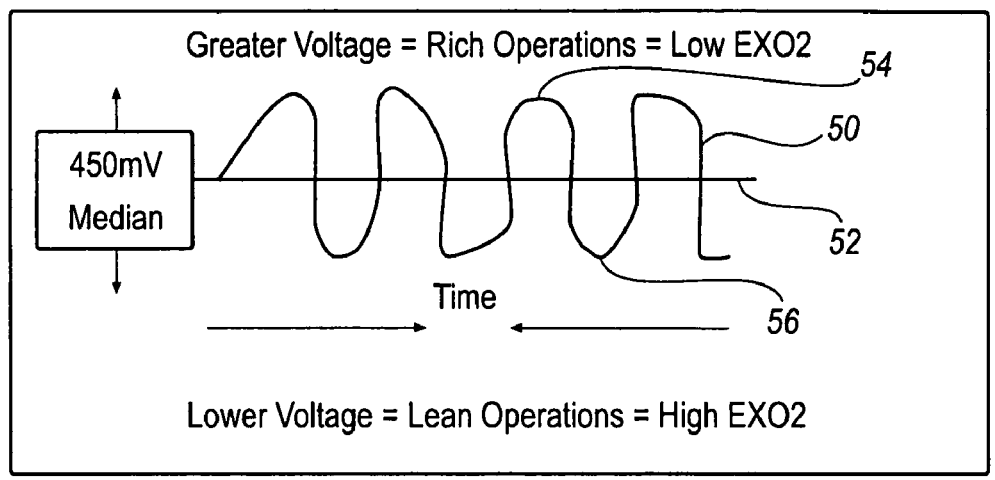
FIG. 2 illustrates a graph showing a graph of oxygen sensor voltage over time as measured between an upper voltage and a lower voltage.

As such, as illustrated in FIG. 2, a typical calibrated oxygen sensor view on an oscilloscope or with a graphing scan will generate a fluctuating voltage line 50 with a generally continuous sinusoidal representation passing through the median voltage level 52 (e.g., 450 mV) between an upper voltage 54 (e.g., 800 mV) and a lower voltage 56 (e.g., 175 mV). FIG. 2 illustrates that a rich mixture with lower amount of oxygen in the exhaust stream results in higher voltages than does a lean mixture with a higher amount of oxygen in the exhaust stream.

Thus, under expected operating conditions, one preferred embodiment of the oxygen sensor 22 should display the following three basic performance criteria if it is operating properly: (1) the oxygen sensor should have a voltage level at a an upper range of 800 mV or more when driven rich (Upper_Voltage); (2) the oxygen sensor should have a voltage level at a lower range of 175 mV or less when driven lean (Lower_Voltage); and (3) the voltage response time from lean to rich and vice versa as shown by the generally sinusoidal representation should be less than approximately 100 milliseconds (mS) (Time_Change_Range).

As discussed in greater detail below, the PCM expects the generated voltage from the oxygen sensor to pass through median within a predetermined period of time. The PCM uses this information to determine the effectiveness and quality of the sensor. If there is no response from the sensor (open) or a constant singular response from the sensor (shorted to ground or power), a diagnostic trouble code (DTC) will be set by the PCM. Also, if the sensor fails to respond to a rich command or lean command within a given amount of time, a sensor performance DTC will be stored in the memory of the PCM.

III. Oxygen Sensor Pre-Validation System Checks

A. Establish Communications

Figure 4:
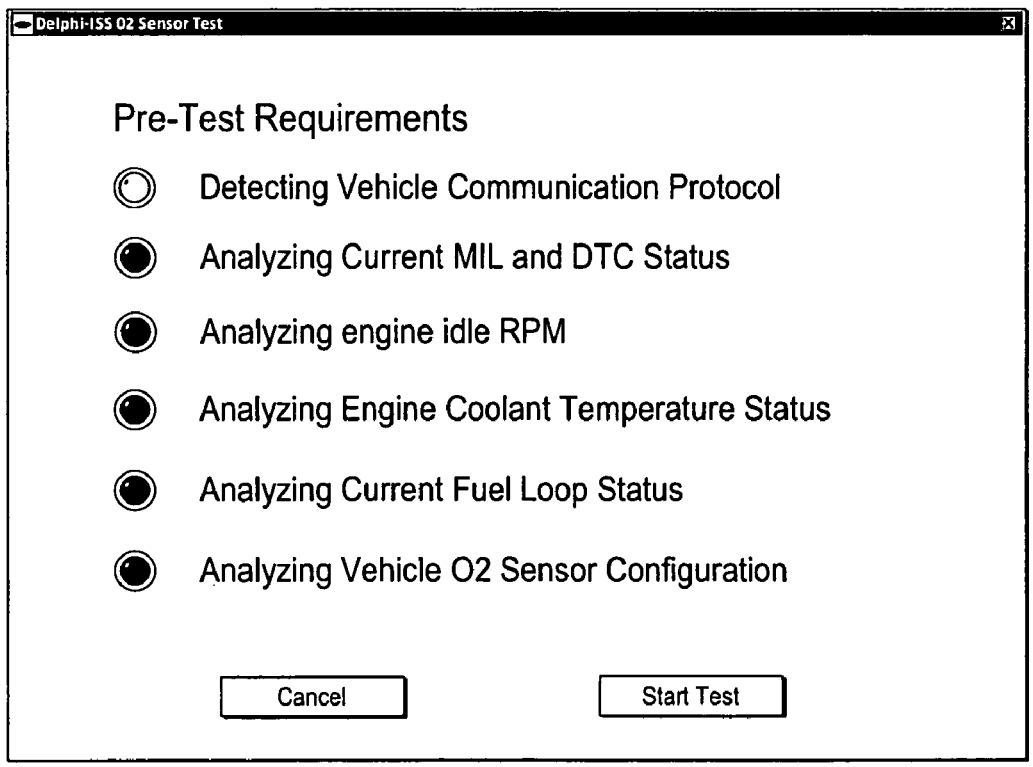
FIG. 4 illustrates a screen shot from the analyzer showing exemplary pre-validation system test requirements.
Figure 3:
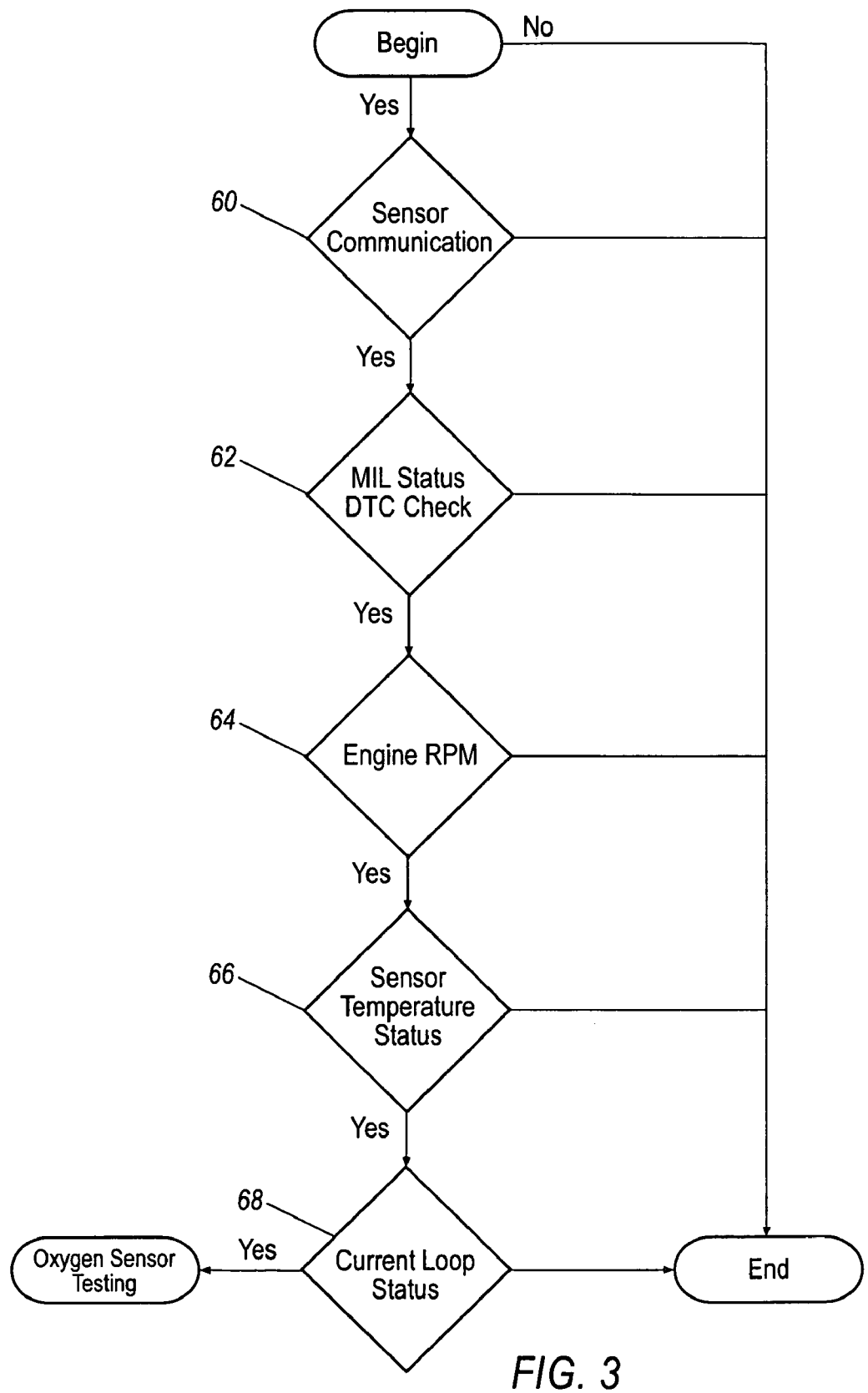
FIG. 3 is a flow chart showing oxygen sensor pre-validation system checks.

The oxygen sensor pre-validation system checks are shown in FIG. 3 with a sample screen short from the analyzer 34 shown in FIG. 4. Prior to conducting diagnostic testing of the oxygen sensor 22, communication with the PCM 30 may be established at point 60 according to Delphi's Integrated Service Solutions (ISS) guidelines. However, establishing communication between the system and the PCM is not limited to the guidelines under Delphi's ISS, and may be established under any system that includes a hardware reset and automatic vehicle communications protocol detection. The establishing of communication will include a hardware reset and automatic vehicle communications protocol detection. This procedure is preferably in compliance with the procedures set forth in SAE document J1979 for automatic protocol detection.

B. Pre-Test Validation and Test Conditioning

Initially, pre-validation testing is performed to determine the status of various systems within the vehicle. Insuring specific conditions have been achieved prior to conducting diagnostic testing of the oxygen sensor 22 prevents the technician from conducting inaccurate diagnostic testing. Moreover, the likelihood of a working oxygen sensor 22 being replaced based upon an incomplete, or incorrect, diagnostic testing of the oxygen sensor is reduced.

Preferably, the analyzer presents a user-interface something like that shown in FIG. 3. If any of the pre-conditions are not satisfied then pre-validation terminates with an error message. If the tests are satisfied then system 20 moves onto oxygen sensor system testing. The pre-conditions include the following:

1. MIL Status and DTC Check

An on-board control module such as the on-board diagnosis (OBD) II system is polled at point 62 for malfunction indicator light (MIL) status and stored diagnostic trouble codes (DTCs) as part of the pre-test conditioning checks. If the MIL is commanded ON, or a DTC is stored other than a code that is designated as an oxygen sensor code, the test will be aborted and the user advised of the trouble code/s. In other words, if a stored DTC is encountered during the PCM inspection sequence that may affect oxygen sensor testing, the fault code will be communicated to the technician through the analyzer and diagnostic testing of the oxygen sensor 22 will be aborted.

The test will instruct the user to repair the reason for the MIL ON or Non-oxygen sensor diagnostic trouble code and retest after the repair. In addition to the examples given above, another example of a potential DTC is a bad connection between a particular sensor and the PCM.

The providing of DTCs through the analyzer permits the technician to fix known problems. Lists of DTCs are available for most carmakers and are known in the art. Once the fault code has been corrected, the technician may repeat the initial pre-validation testing for stored fault codes.

2. Engine RPM

The OBD system is polled for current RPM status at point 64. This is to verify that the engine is running and is a requirement for running the test. If the engine rpm is less than a predetermined RPM, typically between approximately 350 and 400 RPM (Engine_Start_RPM) the user will be presented with a pop up message and instructed to start the engine. The user can either start the engine and continue or "Abort" the test at this time.

3. Sensor Temperature Status

Before an oxygen sensor 22 may be tested as shown at point 66, it must be at a minimum operational temperature. One approach is to have a thermometer associated with the oxygen sensor itself. Another approach is to use a thermometer separate from the oxygen sensor 22, but within the same operational environment of the exhaust gas system. In one embodiment, the sensor may be tested once it is heated up to at least 574 degrees ° F. The thermometer measures the temperature of exhaust gases to make sure that such gases are at the minimum temperature for a predetermined period of time to assure that the sensor itself is at a minimum acceptable operating temperature. A third approach is to measure engine coolant temperature. In one embodiment, the coolant temperature must be a minimum of 70 degrees Celsius (C) to assure that the oxygen sensor 22 itself is at its minimum appropriate operational temperature.

Using one or more approaches for confirming of that the oxygen sensor 22 is at a minimum operational temperature, if the temperature is too low, the technician will be instructed to wait until the appropriate temperature is obtained, and the system will continue to monitor readings until the appropriate conditions are satisfied and no oxygen sensor testing will be undertaken.

More specifically, in one preferred embodiment, the OBD II system is polled using for Engine Coolant Temperature (ECT) (Coolant_Temp). If a status of less than 70° C. is returned, a wait screen will be displayed and the used is instructed to wait until the coolant temperature status of at least 70° C. is achieved. No provision is made to bypass this test condition. The user may select "Cancel" and Abort the test at this point if they so choose.

4. Current Loop Status

Once a proper operational temperature is reached, in one preferred embodiment of the invention, the appropriate on-board vehicle module or system of a vehicle, such as the OBD II system is polled for current fuel-loop status as shown at point 68. Diagnostic testing of the oxygen sensor 22 will only be preformed if a CLOSED LOOP status is achieved. If an OPEN LOOP status is returned, the technician will be informed of the OPEN LOOP status on the screen. The technician will be given an opportunity to wait for the CLOSED LOOP status to be detected. If the technician chooses not to wait for the CLOSED LOOP status, the system will automatically abort diagnostic testing of the oxygen sensor 22. If the technician wishes to wait for the CLOSED LOOP status, the system will continue to monitor readings until the proper conditions are reached. If the CLOSED LOOP status is achieved, the technician will be informed of the success and diagnostic testing of the oxygen sensor will continue.

More specifically, an instructional screen is displayed to the user "Waiting for Closed Loop". In one preferred embodiment, a three (3) minute timer is started and loop status will be checked every 500 mS (0.5) seconds until a CLOSED LOOP status is achieved. If the status is achieved, a screen reporting that CLOSED LOOP has been achieved will be displayed and the test will continue.

If after the timer has expired CLOSED LOOP cannot be achieved, the test will abort and fail for "Closed Loop Status" was not achieved. A list of possible failures will be displayed and the user will be instructed to repair the condition that is keeping the system from entering closed loop and re-run the oxygen sensor test after the repair has been made.

III. Oxygen Sensor Testing

Figure 5:
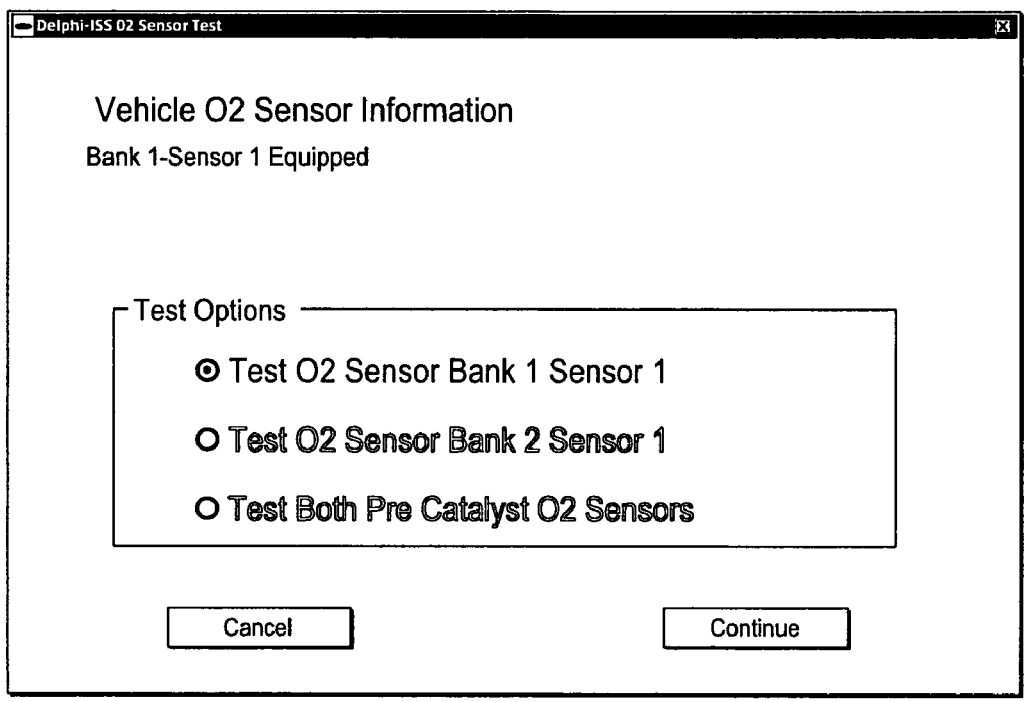
FIG. 5 illustrates a screen shot showing the oxygen sensors for a particular vehicle that are available for testing.

Once pre-validation testing has been successfully conducted, the system will determine the engine configuration and the oxygen sensor 22 arrangement of the vehicle 28. In a preferred embodiment this is accomplished by first issuing a Mode 01 PID 18 request and looking for a valid response from oxygen sensor B2-S1. If a response if not received, an engine 26 with one cylinder bank has been detected and only one sensor test option will be displayed as illustrated in FIG. 5.

If a response is received from the Mode 1 PID 18 request, a two cylinder bank engine configuration has been detected, a flag will be set for a V engine configuration, and test options for Bank 1 and Bank 2 oxygen sensor testing will be presented during the test. A V-engine configuration consists of two cylinder banks set at an angle with respect to one another. Accordingly, two oxygen sensors 22 are required for the two separate cylinder banks.

A. Snap Switch Test

Figure 6:
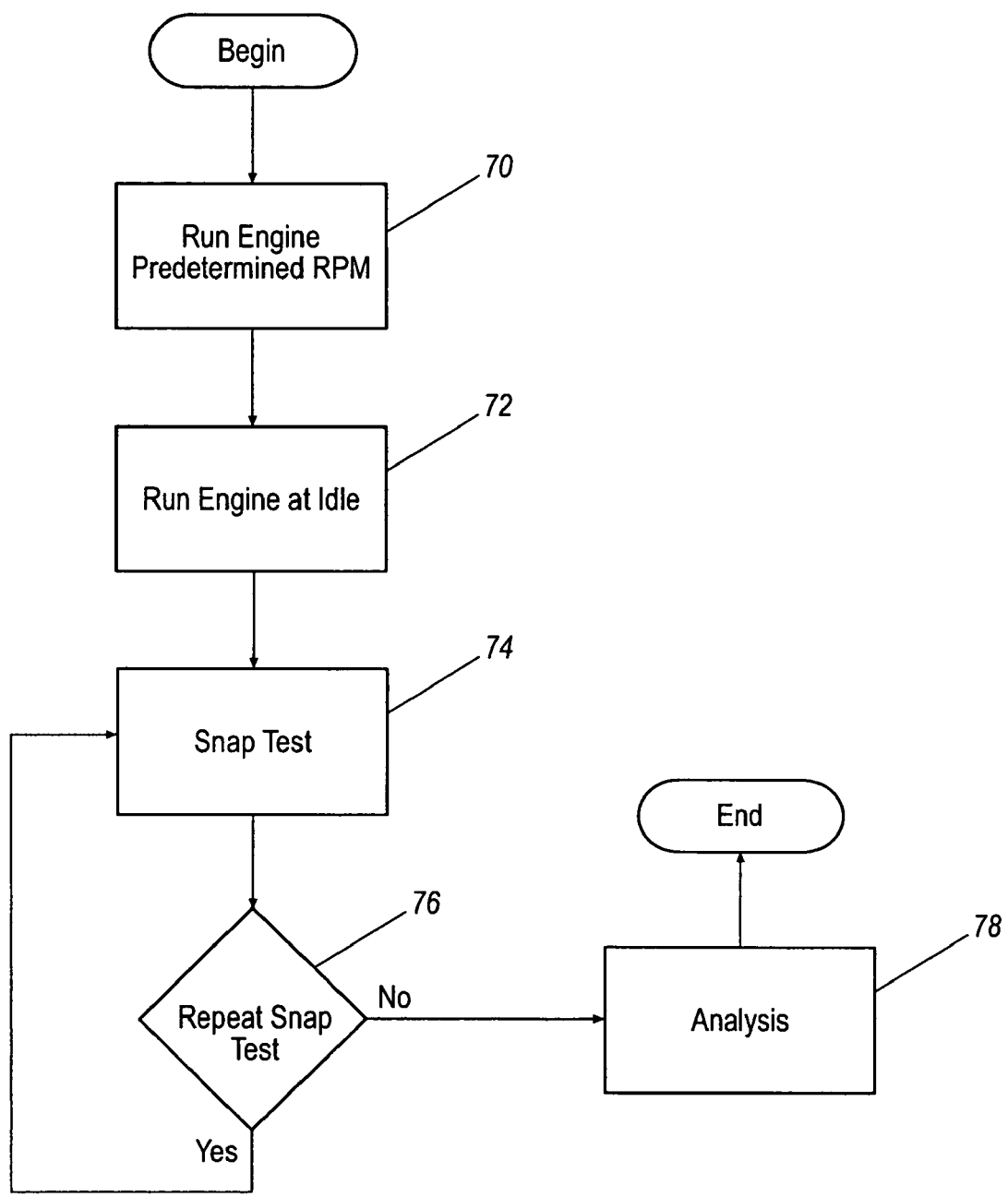
FIG. 6 is a flow chart of a Snap Switch Test for an oxygen sensor.

The Snap Switch Test is usually the first oxygen sensor test performed on a vehicle once the pre-validation tests are completed. The snap switch test is used as a way to test the response time of an oxygen sensor 22. As shown in FIG. 6, the test is conducted using at least a subset of the following:

1. The engine is run at a predetermined RPM for a predetermined period of time to assure oxygen sensor heating and activity as shown at point 70;
2. The engine will be permitted to idle for a predetermined idle time at a predetermined idle RPM as shown by point 72;

3. The throttle is snapped a predetermined number of times at predetermined intervals as shown by point 74 wherein the number of snap intervals is determined by decision point 76; and 4. As shown at point 78, the recorded data is analyzed to measure the response time from lean to rich mixtures using the change between low and high generated voltages.

Figure 7:
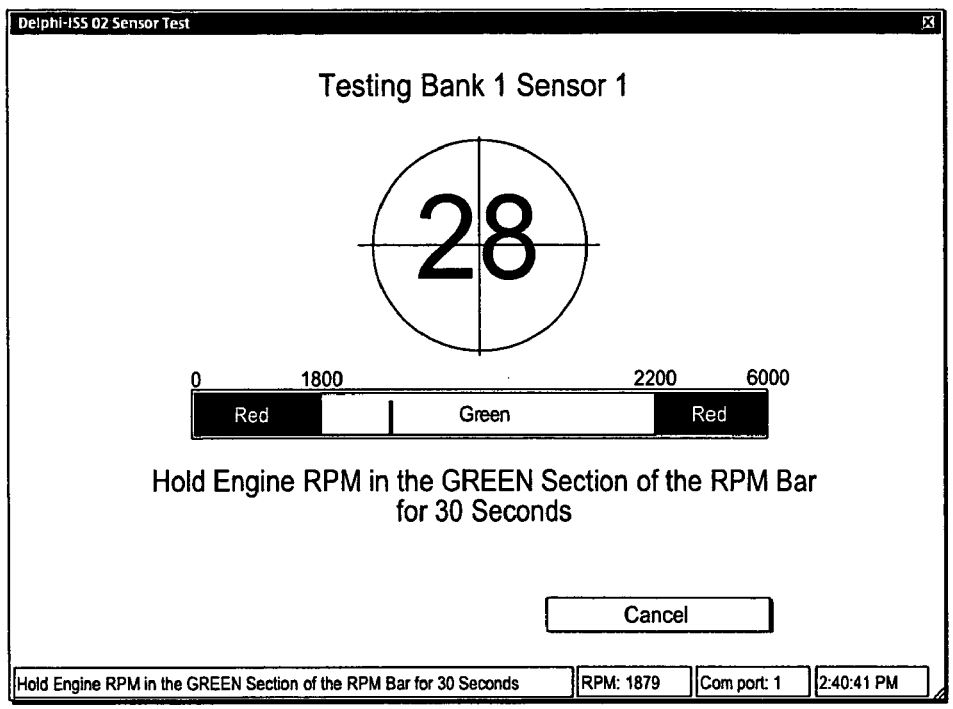
FIG. 7 illustrates a screen shot from the analyzer showing a step of the Snap Switch Test.

More specifically, at the start of the test, the technician will be instructed to run the engine at a predetermined revolutions per minute (RPM) for a predetermined period of time to assure oxygen sensor heating and activity. A screen shot from the analyzer 34 in FIG. 7 shows a countdown timer along with the acceptable range of RPMs that the vehicle may be maintained within.

Figure 8:
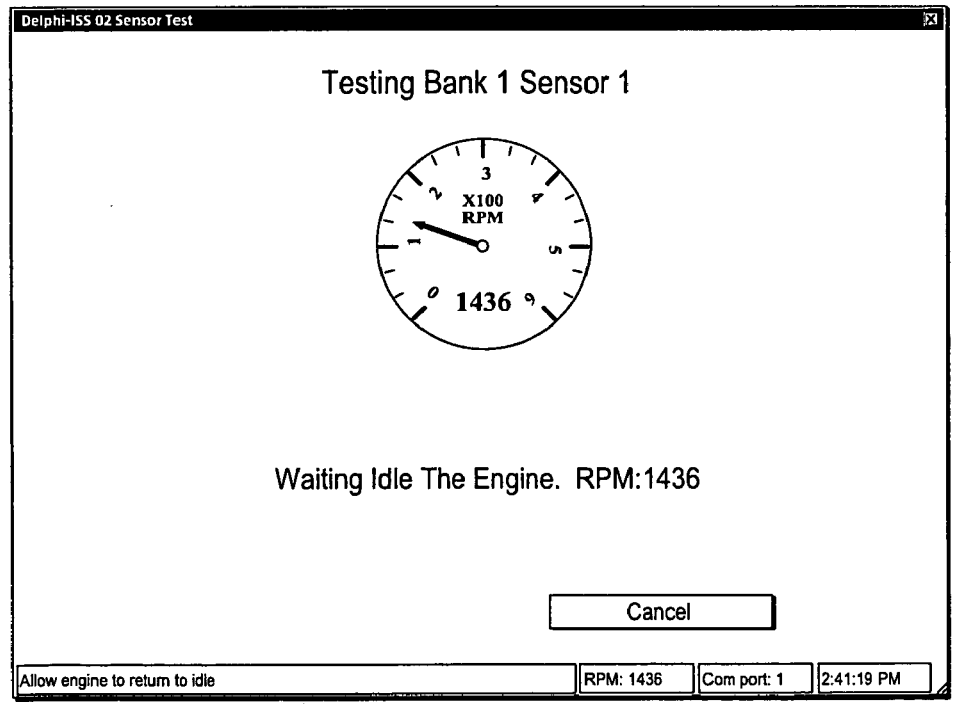
FIG. 8 illustrates a screen shot from the analyzer showing another step of the Snap Switch Test.

After the predetermined time has elapsed at the predetermined RPM the technician will be instructed to let the engine idle for a predetermined idle time and optionally at a predetermined idle RPM. In FIG. 8, a screen shot from the analyzer 34 shows that the idle RPM is illustrated rather than the user having to establish a predetermined idle RPM. Optionally, a visual countdown will be displayed on the screen.

After the predetermined idle time has passed, the technician will be instructed to snap the throttle. The throttle is snapped by way of the throttle sensor. The process of snapping the throttle is repeated for a pre-determined time interval until the predetermined number of throttle snaps is reached (e.g., the throttle is snapped three (3) times at five (5) second intervals).

To assist the technician, in a preferred embodiment the screen of the analyzer will display a visual timer, or countdown, for each step of the test. During the Snap Throttle Switch test, the system collects and analyses the data received from one or more on on-board vehicle control module. When the throttle is snapped, the oxygen sensor 22 should be able to detect the additional amount of oxygen present before the fuel system can react to the throttle change. The voltage of a properly functioning oxygen sensor 22 should switch between approximately a lower voltage and an upper voltage. Additionally, the switch in voltages should occur within a pre-set timeframe. At the end of the test, depending on the response time of the oxygen sensor, a PASS or a FAIL will appear on the display. The technician will have the option of displaying the data in graph format if the technician wishes to view the actual oxygen sensor voltage readings. If the oxygen sensor 22 fails the Snap Throttle Switch test, the technician will be instructed to replace the oxygen sensor. If the oxygen sensor 22 passes the test, the technician will be instructed to continue additional diagnostic testing.

In one embodiment the sensor is a zirconia oxygen sensor 22. Using such a sensor, one preferred set of variables is as follows: The predetermined RPM is approximately two thousand (2000) (HoldRPM_Low) or two thousand five hundred (2500) (HoldRPM_High) and the predetermined period of time is approximately thirty (30) seconds (Hold_Time). The idle time is approximately five (5) seconds (Idle_Time) and the idle RPM is approximately 1000 RPM (IDLERRPM). The predetermined number of times that the throttle is snapped is three (3) (Snap_Number), and the pre-determined interval is approximately five (5) seconds (Snap_Intervals). The upper voltage is approximately 800 mv (Upper_Voltage) when driven rich, the lower voltage is approximately 175 mV (Lower_Voltage) when driven lean, the median voltage is 450 mV (Cross_Voltage) and the switch in voltages should occur within approximately 100 mS (Time_Change_Range).

Figure 9:
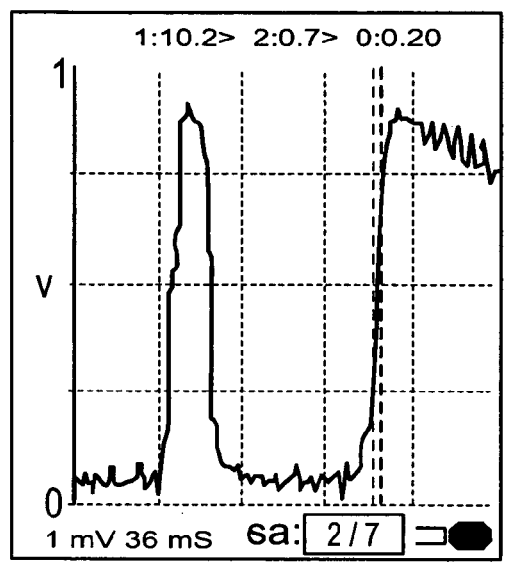
FIG. 9 is a graph with an analysis from the Snap Switch Test showing voltage versus time.

FIG. 9 is a graph that illustrates the switch response time of a good oxygen sensor 22 using the Snap Switch Test. The Y axis illustrates voltage and the X axis illustrates time. In this example the arrow indicates the rush of fresh air the sensor should detect when the throttle is snapped, before the fuel system can react to the throttle change. The two dotted lines indicate the lean/rich transition the sensor should see when the engine controller responds to the lean condition when the throttle is snapped and fuel is delivered.

Figure 10:
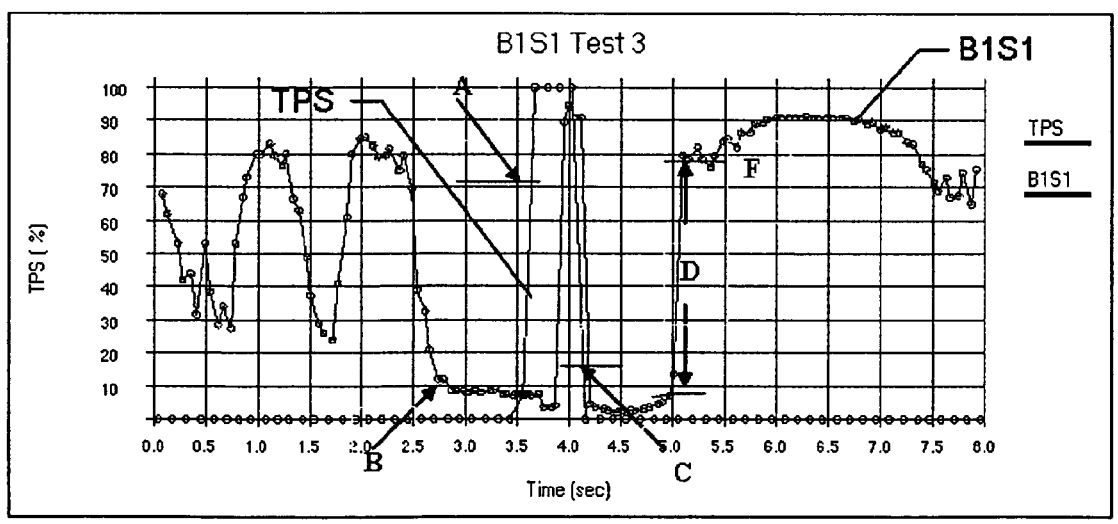
FIG. 10 is a graph with an analysis from the Snap Switch Test showing both voltage and TPS versus time.

In practice the analysis is often more sophisticated. In addition to oxygen sensor data, throttle position sensor (TPS) data is collected from the vehicle at the vehicle bus interface for the same time frame. The data collected is presented in FIG. 10.

The oxygen sensor data collected is analyzed using a Forward—Lean Conditional—summing algorithm that works in the following manner.

First, the data record is analyzed to establish the position in the data where the Throttle Position Sensor (TPS) condition reaches 70% opening. This is indicated in FIG. 8 as "Point A" on the white trace, which represents TPS open percentage.

Next, once data point "A" has been achieved, the lean conditional summing algorithm looks for the lean condition that results from the throttle being rapidly opened. This occurs because when the throttle opens; air rapidly enters the engine because of the negative pressure in the intake and enters the cylinder before the fuel system has time to react and add fuel, hence the oxygen sensor will see this gulp of oxygen rich air which causes the sensor voltage to drop below 175 mV using the exemplary sensor. Data point "C" is the position in the trace where the sensor has seen the fresh air and has reached the point of 175 mV.

Once point "C" has been achieved, the lean-to-rich transition represented by intensity increase "D" needs to be extracted from the trace data. This is accomplished by analyzing the difference between every oxygen sensor data point after data point "C". Once point "C" has been established, the next data point, point "X" is summed opposing "C". If the sum is negative, point "C" is disregarded as the "Lean Conditional" point and, point "X" becomes the base point. Then the next point is summed opposing point "X". This analysis continues until the sum is positive.

Once the trace has begun to transition positive; indicated at point "E", the algorithm sums each consecutive positive data point, adding it to the intensity sum of the trace, until the sum is no longer positive which is indicated by point "F".

Next, once point "F" has been found, the distance between "E" & "F" become the snap switch to be analyzed. Thus, for the illustrated embodiment, the algorithm determines if "D" is at least +600 mV (Voltage_Change_Range) and if the transition occurred in less than 100 mS (Time_Change_Range) according to one example embodiment. If it did, the snap switch for that event has passed.

Preferably, three (3) data recording events are executed during the Snap Switch Test of a sensor. The sensor data must pass the Snap Switch Test in two (2) of the three (3) recorded events to pass the Snap Switch test.

As noted above, after testing, the results of the switch test segment of the test will displayed to the screen with a PASS or FAIL status. If a PASS is displayed, the user will be instructed to CONTINUE to the next test, which in the illustrated embodiment is the Cross Count Cruise Test. If a FAIL is displayed, the user will be instructed to replace the Sensor and retest the system.

B. Cruise Cross Counts Test

Figure 11:
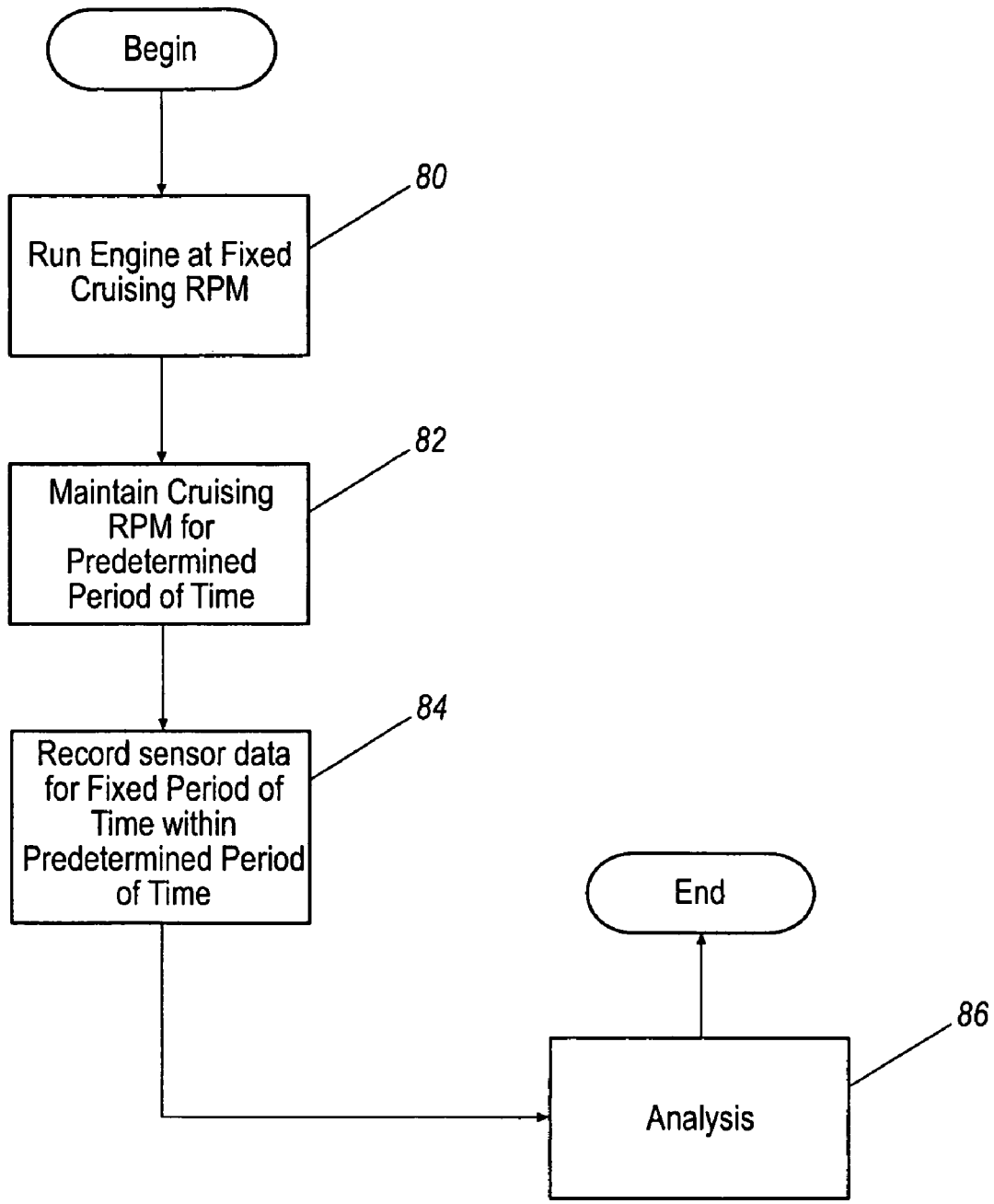
FIG. 11 is a flow chart of the Cruise Cross Counts Test for an oxygen sensor.

FIG. 11 illustrates a second diagnostic test performed on the oxygen sensor 22, the Cruise Cross Count test. The purpose of the Cruise Cross Count test is to determine if a proper cross count status is achieved by the oxygen sensor 22 during a cruising scenario at a fixed RPM.

The test is conducted using at least a subset of the following:

1. The engine is set at a fixed cruising RPM as shown at point 80.
2. The engine is maintained at the fixed cruising RPM for a predetermined period of time as shown at point 82.
3. As shown at point 84, oxygen sensor data is recorded for a fixed period of time, which is less than the predetermined period of time.
3. A determination of cross counts is made for the fixed period of time to determine if a proper cross count status was achieved as shown at point 78.

Figure 12:
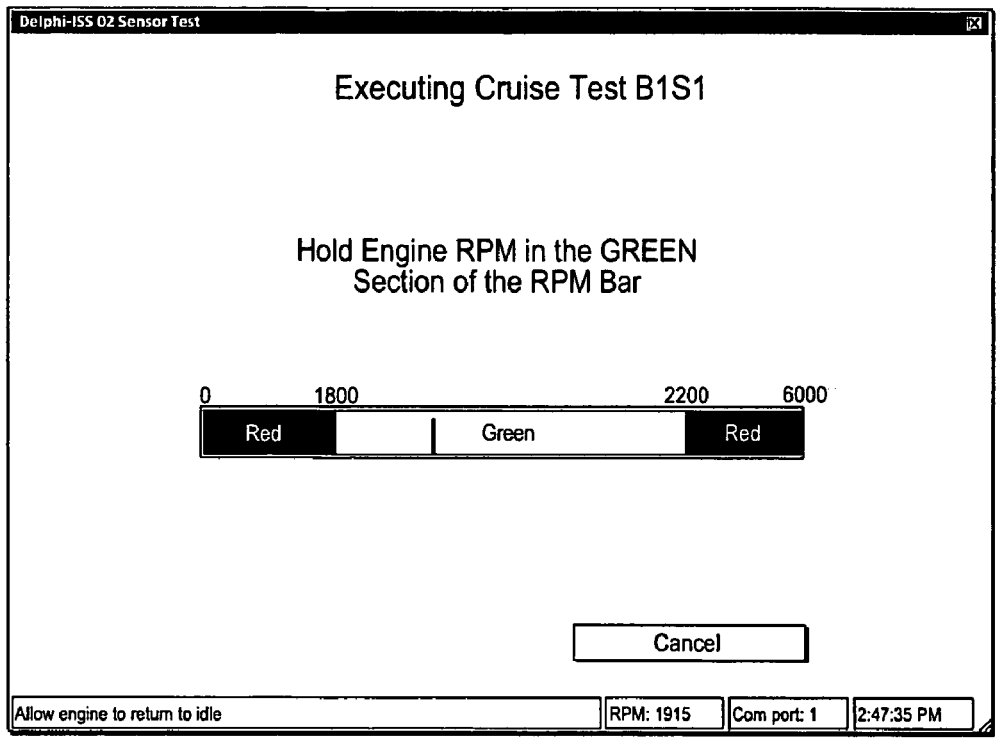
FIG. 12 illustrates a screen shot from a step of the Cruse Cross Counts Test.

More specifically, at the start of the test, the technician will be instructed to run the engine within a range of predetermined revolutions per minute (RPM) for a predetermined period of time. FIG. 12 shows a screen shot presented to a user showing the acceptable range of RPMs that the vehicle may be maintained at while undergoing the test. In contrast to a specific countdown timer, the figure simply says that the test is being executed.

Oxygen sensor data in the form of voltage is recorded for a fixed period of time, which is less than the predetermined period of time. A determination of cross counts is made over the fixed period of time. A cross count occurs when the voltage crosses over a predetermined voltage, which in the disclosed embodiment is the median voltage threshold. Afterward, the system will analyze the results of the collected data.

Preferably, the test results will be displayed in manner similar to the following:

Expected # of Cross Counts per Second: (3–5)
Actual # of Cross Counts per Second: (4)
Results: Pass-Fail (here a "Pass")

Accordingly, the system will display a PASS or a FAIL result depending on the number of cross counts. If a FAIL result is displayed, the technician will also be presented with a list of systems within the vehicle that should be verified before the oxygen sensor 22 is replaced. For example, the fuel system, the ignition system, Exhaust-gas recirculation (EGR) operation, and the air intake and exhaust systems may need to be checked before the oxygen sensor is replaced. As with the Snap Throttle Switch test, if the technician wishes to view the voltage reading of the oxygen sensor 22, the technician will have the opportunity to view the data in graph format.

Finally, a summary report of the diagnostic test will be provided at the completion of the diagnostic testing. The system may be connected to a printer so that the technician will have the opportunity to print any graphs and the summary report if desired.

In one embodiment the sensor is a zirconia oxygen sensor 22. Using such a sensor, one preferred set of variables is as follows: The fixed curising RPM is approximately two thousand (2000) (HoldRPM_Low) or two thousand five hundred (2500) (HoldRPM_High). The predetermined period of time is ten (10) seconds (Total_Countdown_Time). The fixed period of time is five (5) seconds (Cruise_Time) and the beginning and ending points of the fixed period of time are somewhat in the middle of the predetermined period of time. The upper voltage will be at least 800 mV or more when driven rich (Upper_Voltage) and a voltage level below 175 mV when driven lean (Lower_Voltage), the median voltage is 450 mV (Cross Voltage) and the switch in voltages should occur within approximately 100 mS (Time_Change_Range). The cross count of a properly functioning oxygen sensor 22 should range between two (2) to five (5) cross counts per second (Cross_Number) depending on the type of fuel delivery system.

Figure 13:
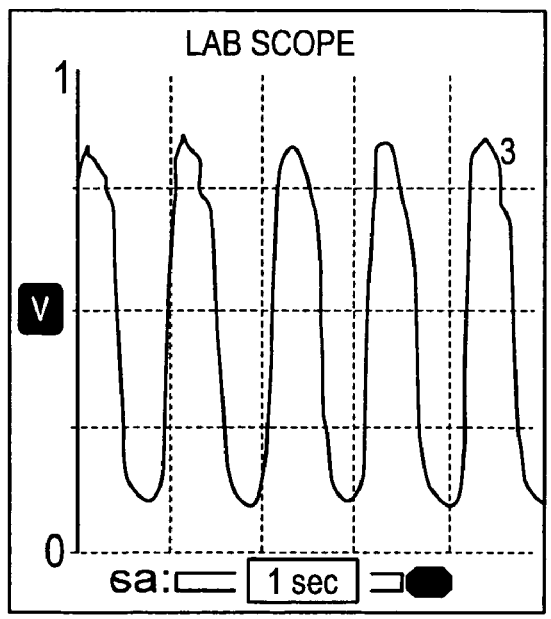
FIG. 13 is a graph with an analysis from the Cruise Cross Counts Test showing voltage versus time.

FIG. 13 is a graph that illustrates the switch response time of a good oxygen sensor 22 using the Snap Switch Test. The Y axis illustrates voltage and the X axis illustrates time. Nine cross-counts are illustrated in the graph.

Figure 14:
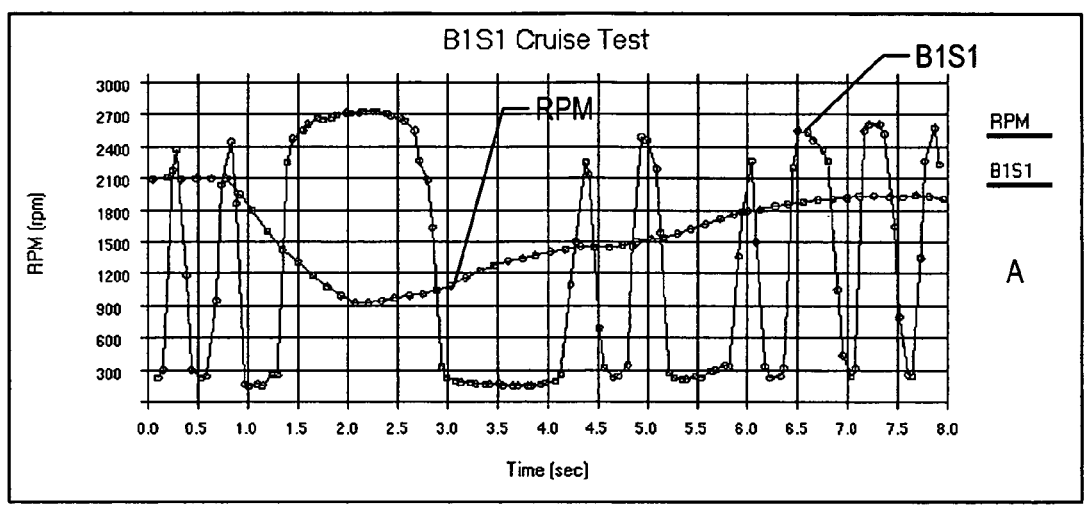
FIG. 14 is a graph with an analysis from the Cruise Cross Counts Test showing both voltage and RPM versus time.

A more detailed graph is shown in FIG. 14 showing both oxygen sensor data and RPM on the Y-Axis versus time. The data is analyzed to identify any transition across the bias median voltage represented by line "A". Once again, any transition across line "A" whether negative or positive in a direction is counted as a transition or "cross count".

If a flag has been set by system 20 designating a V engine configuration during the oxygen sensor detection phase of the test, and the flag has been set from the user selecting "Test Both Sensors" as shown in FIG. 5, the test will be run on Bank 1 Sensor 1 (B1S1) following the procedure discussed above and then re-run for Bank 2 Sensor 1 (B2S1). Alternatively, if the V engine configuration flag has been set during the oxygen sensor detection phase, and the user has selected only sensor, only that sensor will be tested.

IV. Characteristic Table

Different vehicles have different inherent characteristic including dissimilar vehicle fuel systems and the processors that run them. Thus, in practice, the tests that are discussed above have been run on baseline vehicles for which oxygen sensor operation has been confirmed. Using the baseline vehicles and their test results, it is necessary to test different values for certain parameters. This is accomplished in the following manner.

There are a number of different parameters that have been identified as necessary to successfully complete the pre-validation tests as well as both the Snap Switch Test and Cruse Cross Counts Test discussed above. The following table illustrates examples of such parameters

| Parameter Name | Parameter Value (Sample) | Notes |
| --- | --- | --- |
| Coolant_Temp | 70 | Minimum Coolant Temperature degrees Celsius |
| Cross_Number | 2 | Cross number/Second (S) |
| Cross_Voltage | 450 | Cruise Test Cross over voltage/Calibrated Median Bias Voltage |
| Cruise_Time | 5 | Cruise Count Time (S) within Total_Countdown_Time |
| Engine_Start_RPM | 400 | Detect if Engine Starts |
| HoldRPM_High | 2500 | Hold the Engine Speed High Limit |
| HoldRPM_Low | 2000 | Hold the Engine Seed |
| Hold_Time | 30 | Hold Time (S) before Snap Switch Test |
| Idler_Time | 5 | Idle Time (S) |
| IDLERPM | 1000 | Idle the Engine Speed Limit |
| Lower_Voltage | 175 | Maximum Lower Voltage (mV) generated by sensor |
| Sensor_Temp | 574 | Minimum Sensor |

-continued

| Parameter Name | Parameter Value (Sample) | Notes |
|---|---|---|
| | | Temperature (F.) for Testing |
| Snap_Interval | 5 | Snap Interval (S) |
| Snap_Number | 3 | Number of Times Throttle is Snapped |
| Time_Change_Range | 100 | Oxygen Voltage Change Occurred Time Range |
| Total_Countdown_Time | 10 | Total Record Data Time (S) |
| TPSLIMIT | 55 | The TPS limit |
| Upper_Voltage | 800 | Minimum Upper Voltage (mV) generated by sensor |
| Voltage_Change_Range | 625 | Oxygen Voltage Change Limit (mV). |

Of course, various variables can be combined together into a different variable. For example, Voltage_Change_Range may often be simply the subtraction of Lower_Voltage from Upper_Voltage although in some embodiments, its value may be less (e.g., 600 mV as opposed to 625 mV). Each table that is modified to support the testing of a vehicle platform will be given a unique identifier and stored in the C-Table database of FIG. 1. The necessary testing input parameters will be given to the technician or directly to the PCM using the analyzer and the results compared to the test output parameters based on the test results. Ideally, the testing input parameters would be the same from vehicle model to vehicle model.

In operation, the DS platform establishes a unique identifier for each combination of Year, Make, Model and Sub Model of vehicle for sale in North America since 1996. This is based on the Automotive Aftermarket Industry Association identification (AAIA_ID) database that resides on the Delphi-ISS Backend SQL server 40, shown as a separate computer system although only one server may be required under some embodiments. Similar standards are used in other parts of the world.

When an oxygen sensor test is run, the first action is to go to the database and ID the characteristic table for that vehicle as identified in the AAIA_ID table. Then the correct table is downloaded from the C_TABLE database and loaded as the characteristics for the test to determine if the test is either a PASS or FAIL.

Once the test is completed the results can be stored on the analyzer 34, locally at the location where the analyzer is used, or at a remote location such as where the server 40 is located.

It should be understood that the aforementioned and other various alternatives to the embodiments of the invention described herein may be employed in practicing the invention. It is intended that the following claims define the scope of the invention and that the method and apparatus within the scope of these claims and their equivalents be covered thereby.

What is claimed is:

1. A diagnostic testing system for a vehicle comprising:
an analyzer having a user interface;
a communications link between said analyzer and said vehicle to obtain data from said oxygen sensor and engine throttle position obtained generally concurrently with said data from said oxygen sensor, said data from said oxygen sensor includes a voltage between an upper voltage and a lower voltage in a generally sinusoidal manner over time;
a diagnostic heuristic to analyze said data and confirm proper operation of said sensor, said diagnostic heuristic comprising correlating engine throttle position with said data from said oxygen sensor over said time and measuring a first time period between said upper voltage and said lower voltage; and
an output generated by said diagnostic heuristic to said user interface including the results generated by said diagnostic heuristic.

2. A diagnostic testing system as in claim 1, wherein a cross-count voltage is established between said upper voltage and said lower voltage, and wherein a second time period is set and the number of counts measured where said voltage matches said cross-count voltage within said second time period.

3. A diagnostic testing system as in claim 2, further includes engine RPM obtained generally concurrently with said data from said oxygen sensor such that said engine RPM can be correlated with said data from said oxygen sensor over said second time period.

4. A diagnostic testing system as in claim 1, wherein said data is collected over a predetermined time for use by said diagnostic heuristic.

5. A diagnostic testing system as in claim 1, wherein said diagnostic heuristic includes a set of instructions presented through said user interface.

6. A diagnostic testing system as in claim 5, wherein said set of instructions includes pre-validation system check.

7. A diagnostic testing system for a running vehicle having an internal combustion engine and an oxygen sensor within an exhaust stream of said internal combustion engine, comprising:
an analyzer having a user interface;
a communications link between said analyzer and said vehicle to obtain data from said oxygen sensor, and wherein said data from said oxygen sensor includes a voltage, said voltage ranging between an upper voltage and a lower voltage in a generally sinusoidal manner;
a diagnostic heuristic to analyze said data and confirm proper operation of said sensor, said diagnostic heuristic comprising a first test to measure a first time period between said upper voltage and said lower voltage and to determine whether said first time period is within a pre-set threshold and, if said first time period is within said pre-set threshold, a second test to establish a cross-count voltage between said upper voltage and said lower voltage and to determine a number of counts where said voltage matches said cross-count voltage within a second time period such that said sensor passes a second test if said number of counts is within said pre-set threshold; and
an output generated by said diagnostic heuristic to said user interface.

8. A diagnostic testing system as in claim 7, wherein prior to said first test, said system includes pre-test validation, said pre-test validation including confirming sensor communication; module indicator light and diagnostic trouble code analysis; engine RPM; and sensor temperature.

9. A diagnostic testing system as in claim 8, wherein said sensor temperature is determined as a function of coolant temperature.

10. A method for diagnostic testing of an oxygen sensor within a vehicle, the method comprising:

configuring a user interface in communication with a software system;

configuring a communications link in communication with said software system;

said software system communicating with said oxygen sensor;

conducting a pre-validation test using said software system; and conducting a diagnostic test of said oxygen sensor using said software system, said diagnostic test comprising correlating engine throttle position with data from said oxygen sensor and measuring a first time period between an upper voltage and a lower voltage, and wherein said diagnostic test further includes the steps of:

setting a cross-count voltage;

determining a cross count value for said oxygen sensor based upon the number of times said voltage crosses said cross-count voltage over said first time period; and comparing said cross count value to a pre-set threshold to confirm operation of said sensor.

11. The method of claim 10, wherein said pre-validation test further includes configuring an interface between said software system and an on-board vehicle computer system and testing for stored trouble codes in said on-board vehicle computer system.

12. The method of claim 10, wherein said pre-validation test further includes configuring an interface between said software system and an on-board vehicle computer system and testing for sensor temperature.

13. The method of claim 10, wherein said pre-evaluation test includes determining sensor temperature using engine coolant temperature.

14. The method of claim 10, wherein said diagnostic testing of said oxygen sensor further includes collecting a plurality of voltage readings of said oxygen sensor over a set time period.

15. A method of claim 14, wherein said diagnostic testing of said oxygen sensor further includes the steps of:

measuring the time for said voltage to move from said upper voltage to said lower voltage or from said lower voltage to said upper voltage; and comparing the time to a pre-set threshold to confirm operation of said sensor.

* * * * *